(12) United States Patent  (10) Patent No.: US 9,222,908 B2
Daniels et al.  (45) Date of Patent: *Dec. 29, 2015

(54) DEVICE AND METHOD FOR DETECTING REDOX REACTIONS IN SOLUTION

(71) Applicant: Intel Corporation, Santa Clara, CA (US)

(72) Inventors: Jonathan S. Daniels, Palo Alto, CA (US); Oguz H. Elibol, Palo Alto, CA (US); Grace M. Credo, San Mateo, CA (US); Xing Su, Cupertino, CA (US)

(73) Assignee: INTEL CORPORATION, Santa Clara, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 13/839,564

(22) Filed: Mar. 15, 2013

(65) Prior Publication Data

US 2014/0083866 A1    Mar. 27, 2014

Related U.S. Application Data

(63) Continuation-in-part of application No. 13/628,728, filed on Sep. 27, 2012, now Pat. No. 8,741,117.

(51) Int. Cl.
*G01N 27/30* (2006.01)
*B82Y 30/00* (2011.01)
*G01N 27/327* (2006.01)

(52) U.S. Cl.
CPC ............... *G01N 27/30* (2013.01); *B82Y 30/00* (2013.01); *G01N 27/3277* (2013.01); *Y10S 977/734* (2013.01); *Y10S 977/742* (2013.01)

(58) Field of Classification Search
CPC ......... G01N 27/30; G01N 33/68; B82Y 5/00; B82Y 15/00; Y10S 977/852; Y10S 977/733; Y10S 977/72; Y10S 977/721
See application file for complete search history.

(56) References Cited

U.S. PATENT DOCUMENTS

| | | | |
|---|---|---|---|
| 4,168,442 | A | 9/1979 | Satou |
| 7,172,922 | B2 | 2/2007 | Benjamin et al. |
| 7,304,674 | B2 | 12/2007 | Mentzer et al. |
| 7,342,212 | B2 | 3/2008 | Mentzer et al. |
| 8,093,636 | B2 | 1/2012 | Park |
| 2003/0022150 | A1 | 1/2003 | Sampson et al. |
| 2010/0221846 | A1 | 9/2010 | Widdershoven |
| 2010/0300899 | A1 | 12/2010 | Levine |
| 2011/0065588 | A1 | 3/2011 | Su et al. |

OTHER PUBLICATIONS

Anderson et al., 12MTC 2008, IEEE Confer., May 2008.
Daniels et al., Electroanalysis 19, 2007, No. 12, 1239-1257.

(Continued)

*Primary Examiner* — Jennifer Dieterle
(74) *Attorney, Agent, or Firm* — Pillsbury Winthrop Shaw Pittman LLP

(57) ABSTRACT

Described herein is a device comprising: a plurality of first reaction electrodes arranged in an array, the plurality of first reaction electrodes configured to be exposed to a fluid and having a capacitance; first circuitry configured to controllably set the plurality of first reaction electrode to a predetermined voltage and allow the capacitance of the plurality of first reaction electrode to charge or discharge through the fluid; and second circuitry configured to measure a rate of charging or discharging of the capacitance of the plurality of first reaction electrodes. Also described herein is a method of using this device to sequence DNA.

18 Claims, 17 Drawing Sheets

(56) References Cited

OTHER PUBLICATIONS

Anderson et al., Journal of Stellar EE315 Circuits.

Anderson et al., IEEE Transactions on Crcuits and Systems-I: Regular Papers, vol. 55, No. 11, Dec. 2008.
Daniels, Thesis, Mar. 2010.
Prakash et al., IEEE Sensors Journal, vol. 7, No. 3, 2007.
Abbas El Gamal et al., CMOS Image Sensors, IEEE Circuits & Devices Magazine, May/Jun. 2005, pp. 6-20.

DEVICE AND METHOD FOR DETECTING REDOX REACTIONS IN SOLUTION

CROSS-REFERENCE TO RELATED APPLICATIONS

This application is a continuation-in-part of U.S. patent application Ser. No. 13/628,728, filed on Sep. 27, 2012, the disclosure of which is hereby incorporated in its entirety.

Reference is made to commonly owned and co-pending U.S. application Ser. No. 12/655,578 titled "Nanogap Chemical and Biochemical Sensors," filed Dec. 31, 2009, now pending; U.S. patent application Ser. No. 11/226,696, titled "Sensor Arrays and Nucleic Acid Sequencing Applications," filed Sep. 13, 2005, now pending; which is a continuation-in-part application that claims the benefit of U.S. patent application Ser. No. 11/073,160, titled "Sensor Arrays and Nucleic Acid Sequencing Applications," filed Mar. 4, 2005; U.S. patent application Ser. No. 11/967,600, titled "Electronic Sensing for Nucleic Acid Sequencing," filed Dec. 31, 2007 now pending; U.S. patent application Ser. No. 12/319,168, titled "Nucleic Acid Sequencing and Electronic Detection," filed Dec. 31, 2008, now pending; U.S. patent application Ser. No. 12/459,309, titled "Chemically Induced Optical Signals and DNA Sequencing," filed Jun. 30, 2009, now pending; U.S. patent application Ser. No. 12/655,459, titled "Solid-Phase Chelators and Electronic Biosensors," filed Dec. 30, 2009, now pending; U.S. patent application Ser. No. 12/823,995, titled "Nucleotides and Oligonucleotides for Nucleic Acid Sequencing," filed Jun. 25, 2010, now pending; U.S. patent application Ser. No. 12/860,462, titled "Nucleic Acid Sequencing," filed Aug. 20, 2010, now pending; the disclosures of which are incorporated herein by reference in their entirety. Appropriate components for device/system/method/process aspects of the each of the foregoing U.S. patents and patent publications may be selected for the present disclosure in embodiments thereof.

BACKGROUND

DNA sequencing is the process of reading the nucleotide bases in a DNA molecule. It includes any method or technology that is used to determine the order of the four bases—adenine, guanine, cytosine, and thymine—in a strand of DNA.

Knowledge of DNA sequences is useful for basic biological research, and in numerous applied fields such as diagnostic, biotechnology, forensic biology, and biological systematics. The advent of DNA sequencing has accelerated biological research and discovery. The rapid speed of sequencing attained with modern DNA sequencing technology has been instrumental in the sequencing of the human genome, in the Human Genome Project. Related projects, often by scientific collaboration across continents, have generated the complete DNA sequences of many animal, plant, and microbial genomes.

New development in the medical field (e.g., personalized medicine) and basic biological research (e.g., animal or plant genome projects) calls for rapid sequencing of large number (e.g., above 10,000) of DNA fragments in a practical period of time (e.g., several hours to several days), which is usually referred to as a high-throughput sequencing. Traditional chemistry-based and optic-based DNA sequencing methods such as the Maxam-Gilbert method and Chain-termination methods suffer from their requirements of complex sample preparation and slow rate of base detection, and are generally unsuitable in these applications.

Exemplar high-throughput sequencing techniques include Massively Parallel Signature Sequencing (MPSS) developed by Lynx Therapeutics, Polony sequencing developed by Prof. George Church at Harvard University, parallelized pyrosequencing developed by 454 Life Sciences (now Roche Diagnostics), SOLiD sequencing developed by Applied Biosystems (now Life Technologies), pH-based semiconductor sequencing developed by Ion Torrent (now Life Technologies), nanopore sequencing, etc.

DETAILED DESCRIPTION

A DNA molecule may be sequenced by detecting reaction products from incorporation of individual nucleotides into a polynucleotide chain complementary to the DNA molecule or cleavage of individual nucleotides from the DNA molecule. Various enzymes (e.g., polymerase, deoxyribonuclease) may be used to facilitate the incorporation or cleavage.

One method to detect these reaction products is electrochemistry. Electrochemistry is a branch of chemistry that studies chemical reactions which take place in a solution at the interface of an electron conductor (a metal or a semiconductor) and an ionic conductor (the electrolyte), and which involve electron transfer between the electrode and the electrolyte or species in solution. When the reaction products undergo redox reactions in an electrochemistry cell, electrical signatures (e.g., cyclic voltammogram) of the reaction products may be used to identify them. For example, the reaction products may be those released from incorporation of chemically-modified nucleotides into DNA, as described in U.S. patent application Ser. No. 11/967,600, titled "Electronic Sensing for Nucleic Acid Sequencing," which is hereby incorporated by reference in its entirety.

Figure 1A:
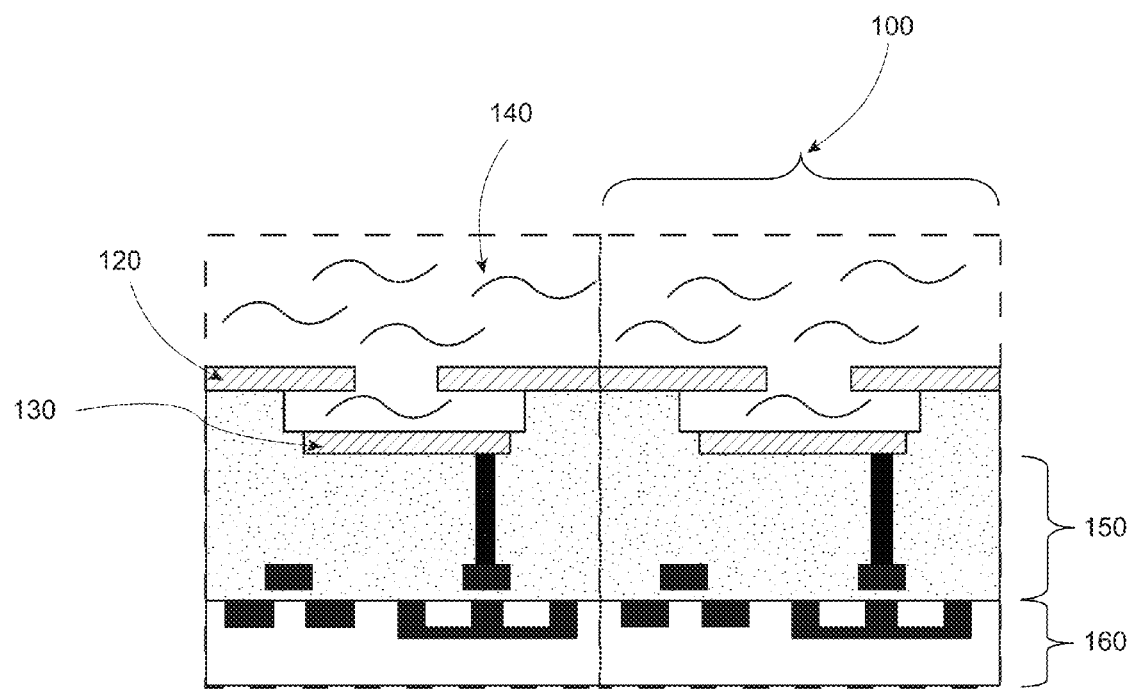
FIG. 1A shows a schematic cross section of a device according to an embodiment.

FIG. 1A shows a schematic cross section of a device according to an embodiment. The device includes an array of unit cells 100. In at least one unit cell, the device has a first reaction electrode 130 and a second reaction electrode 120, preferably both fabricated on a substrate and electrically isolated from each other. The reaction electrodes 130 and 120 are configured to be exposed to a fluid 140. The device may further have transistors 160 in the unit cells (preferably 10 transistors or less in each unit cell, further preferable 3 transistors or less in each unit cell) and interconnect 150. The interconnect 150 electrically connects at least one (e.g., the first reaction electrode 130) of the reaction electrodes 130 and 120 to the transistors 160. The transistors 160 may be configured to measure electrical current through at least one of (e.g., the first reaction electrode 130) of the reaction electrodes 130 and 120. A unit cell may comprise sensors such as the first reaction electrode 130, and circuitry dedicated to the sensors.

Figure 1B:
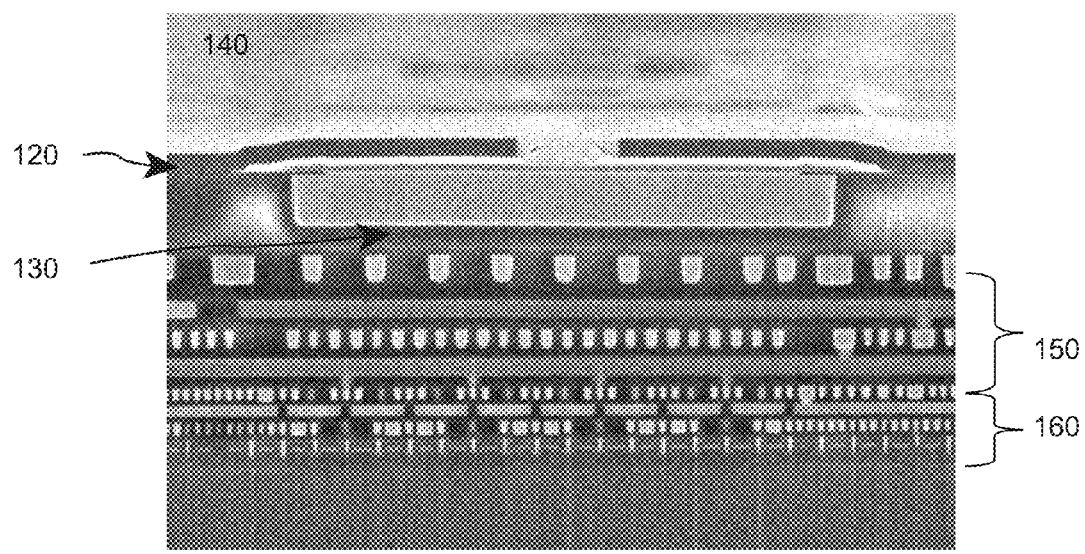
FIG. 1B shows a cross section image of the device of FIG. 1A obtained using scanning electron microscopy.

FIG. 1B shows a cross section image of the device of FIG. 1A obtained using scanning electron microscopy. The gap between reaction electrodes 120 and 130 is preferably small, such as from 1 nm to 100 nm (a "nanogap").

Figure 2A:
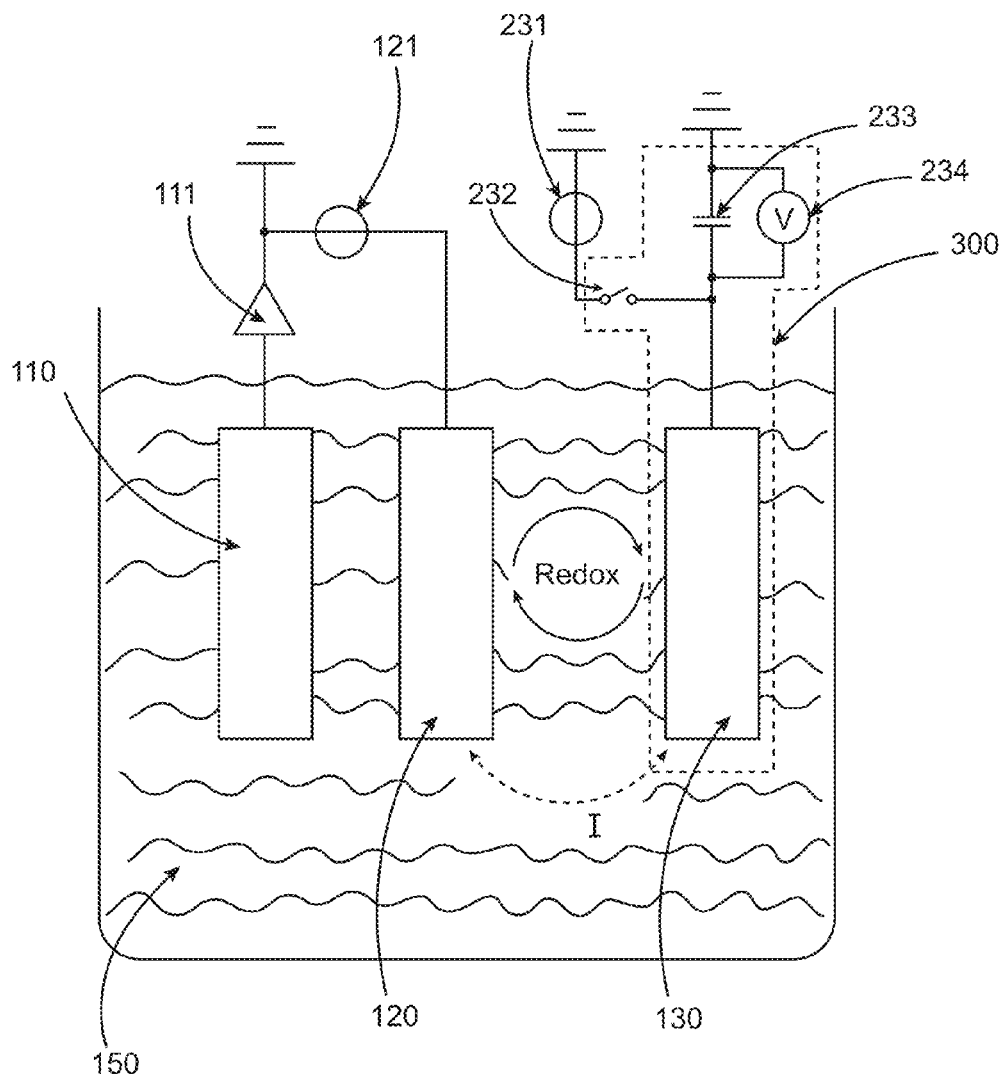
FIG. 2A schematically shows circuits in a unit cellunit cell of the device in FIGS. 1A and 1B and the functions of the circuits.

FIG. 2A schematically shows circuits 300 in a unit cell 100 of the device in FIGS. 1A and 1B and the functions of the circuits. According to an embodiment, electrical current through an electrode may be measured by measuring the rate of charging or discharging of capacitance of that electrode. For example, electrical current through the first reaction electrode 130 may be measured by measuring the rate of charging or discharging of capacitance 233 of the first reaction electrode 130. Although the capacitance 233 of the first reaction electrode 130 is depicted in FIG. 2A as a capacitor separate from the capacitance, it need not comprise a physical capacitor component, but a combination of self-capacitance of the first reaction electrode 130 and capacitance of the interface between the first reaction electrode 130 and the fluid 150. The fluid 150 may be a solution, e.g., aqueous solution or non-aqueous solution. The fluid 150 may be a gaseous phase. The fluid 150 may also be a molten electrolyte such as molten salt.

The circuitry connected to the first reaction electrode 130 as depicted in FIG. 2A is one example that can be used to measuring the rate of charging or discharging of the capacitance 233. In an embodiment, switch 232 is closed to connect the first reaction electrode 130 to a bias source 231. At this state, the voltage on the first reaction electrode 130 is at the voltage of the bias source 231, denoted as $V_0$. The switch 232 may be any circuitry that can electrically connect and disconnect the first reaction electrode 130 to the bias source 231. For example, the switch 232 may be a toggle switch, a relay or a transistor. After the switch 232 is opened to disconnect the first reaction electrode 130 from the bias source 231, redox reactions (electron transfer between the electrode and a chemical species in the solution) occurring at the first reaction electrode 130 start to charge or discharge the capacitance 233 and as a result the voltage of the first reaction electrode 130 deviates from $V_0$. The rate of charging and discharging of the capacitance 223 can be derived from the change of the voltage of the first reaction electrode 130. The voltage of the first reaction electrode 130 may be measured using any suitable circuitry 234. Circuitry 234 is not limited to a voltmeter. In an embodiment, the circuitry 234 may comprise A/D converter. In an embodiment, the circuitry 234 may comprise a buffer. The buffer may drive an A/D converter shared with other electrodes.

Figure 2B:
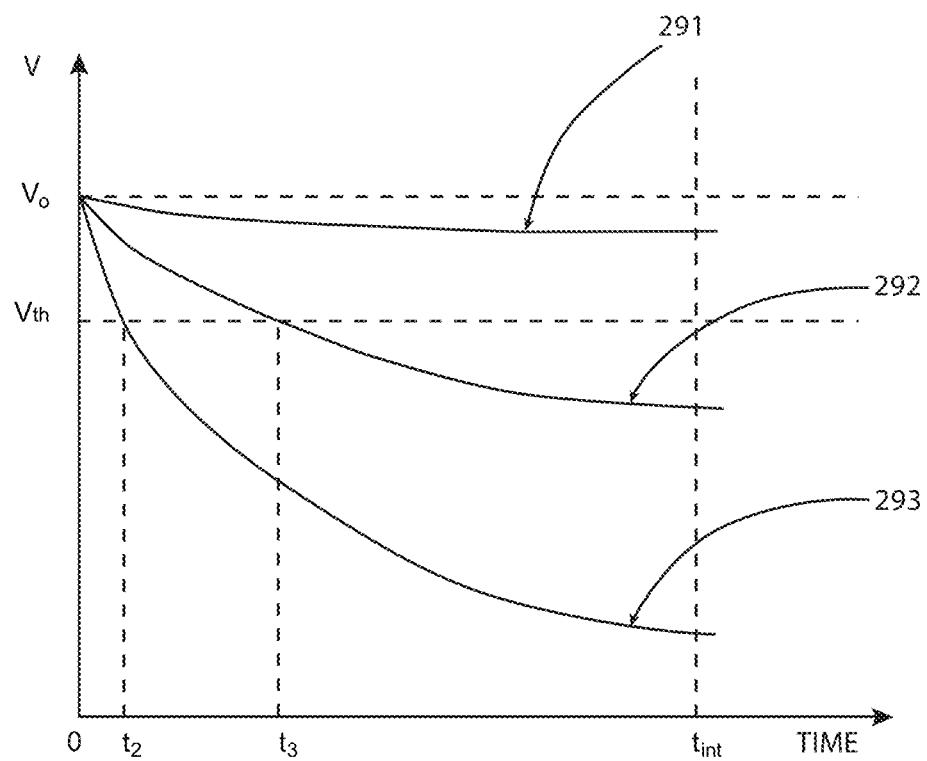
FIG. 2B shows an exemplary graph of the voltage of one of the three electrodes as a function of time, when the redox reaction discharges the capacitance of that electrode.
Figure 2C:
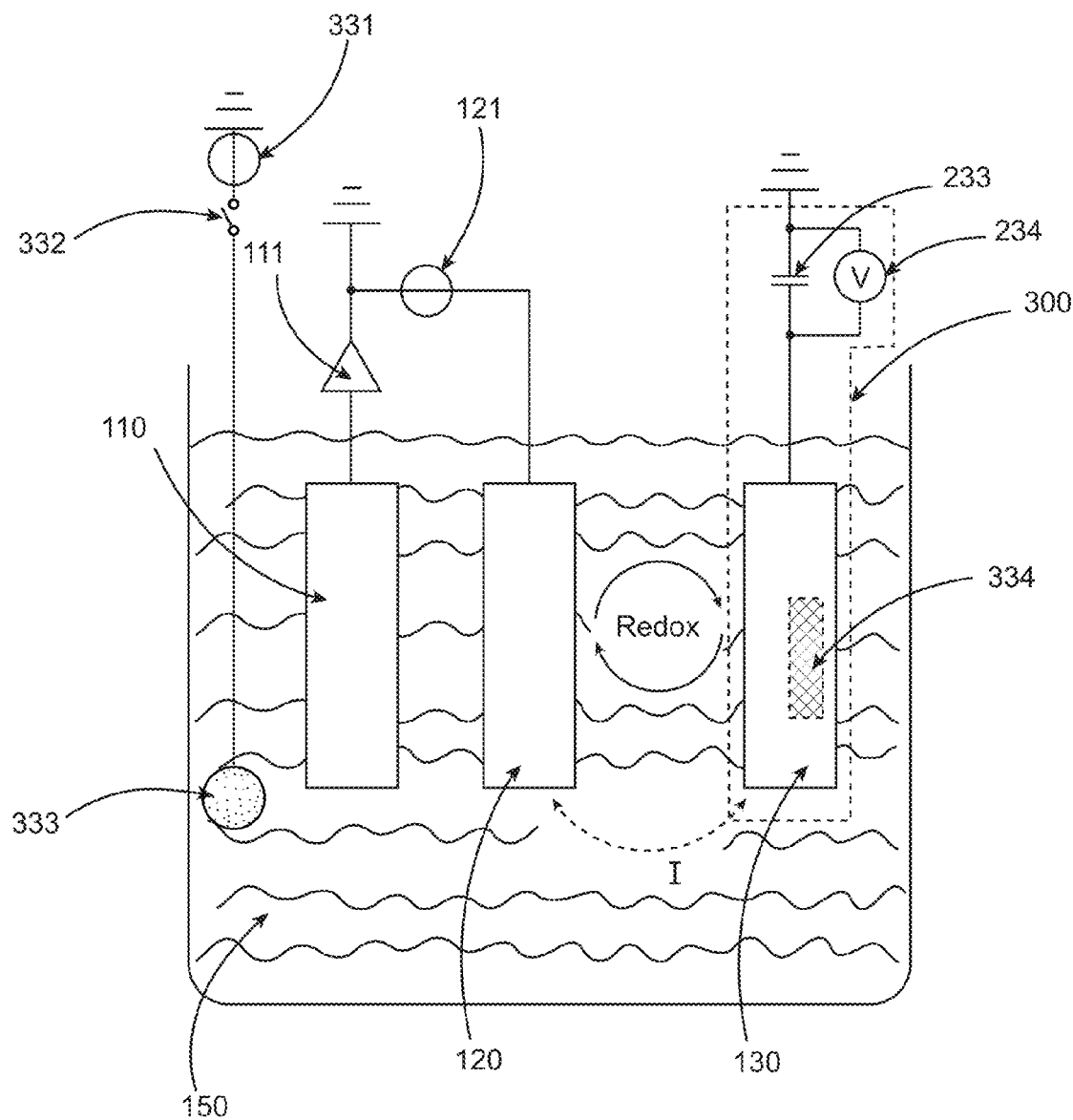
FIG. 2C schematically shows alternative circuits in a unit cellunit cell of the device in FIGS. 1A and 1B and the functions of the circuits.

The circuitry connected to the first reaction electrode 130 as depicted in FIG. 2C is another example that can be used to measuring the rate of charging or discharging of the capacitance 233. In an embodiment, switch 332 is closed to connect a charging electrode 333 disposed in the fluid 150 to a bias source 331. The voltage on the charging electrode 333 may affect the potential of the fluid 150 which affects the voltage on the first reaction electrode 130. At this state, the voltage on the first reaction electrode 130 is at a voltage, denoted as $V_0$. The switch 332 may be any circuitry that can electrically connect and disconnect the charging electrode 333 to the bias source 331. In one embodiment, the bias source 331 may output more than one voltages. For example, the switch 332 may be a toggle switch, a relay or a transistor. After the switch 332 is opened to disconnect the charging electrode 333 from the bias source 331, redox reactions (electron transfer between the electrode and a chemical species in the solution) occurring at the first reaction electrode 130 start to charge or discharge the capacitance 233 and as a result the voltage of the first reaction electrode 130 deviates from $V_0$. The rate of charging and discharging of the capacitance 223 can be derived from the change of the voltage of the first reaction electrode 130. The voltage of the first reaction electrode 130 may be measured using any suitable circuitry 234. Circuitry 234 is not limited to a voltmeter. In an embodiment, the circuitry 234 may comprise A/D converter. In an embodiment, the circuitry 234 may comprise a buffer. The buffer may drive an A/D converter shared with other electrodes. Although the charging electrode 333 is depicted as a separate electrode from electrodes 110 and 120, the charging electrode 333 may be one or both of electrodes 110 and 120.

FIG. 2B shows an exemplary graph of the voltage of the first reaction electrode 130 as a function of time, when the redox reaction discharges the capacitance 233. The more molecules undergo redox reactions in the vicinity of the first reaction electrode 130, the greater the rate of charging or discharging of the capacitance 233. For example, trace 291 in FIG. 2B shows discharge of the capacitance 233 when essentially no molecules undergo redox reactions in the vicinity of the first reaction electrode 130. The slight drop of the voltage on the first reaction electrode 130 is due to leakage current through the fluid 150 and/or leakage current from the circuitry 231 and/or 234. Traces 292 and 293 in FIG. 2B show discharge of the capacitance 233 when some molecules undergo redox reactions in the vicinity of the first reaction electrode 130. Trace 293 shows a greater rate of discharge that trace 292 because more molecules undergo redox reactions in the vicinity of the first reaction electrode 130 when trace 293 is recorded than when trace 292 is recorded. The rate of discharge may be measured directly (e.g., the slope of the traces in FIG. 2B) or by any other suitable techniques. For example, the rate of discharge may be measured by the amount of voltage change from $V_0$ at a time point $t_{int}$ after the first reaction electrode 130 disconnects from the bias source 231 or after the charging electrode 333 disconnects from the bias source 331. In alternative, to reduce drift or noise in circuitry 234, switch 232 or 332 can be closed at a time just after $t_{int}$, resetting the voltage of the first reaction electrode 130 to $V_0$, and the rate of discharge may be measured by the difference between the voltage at $t_{int}$ and the voltage after the reset. In another alternative, the rate of discharge may be measured by the amount of time for the voltage of the first reaction electrode 130 to change from $V_0$ by a predetermined amount to a voltage $V_{th}$ after the first reaction electrode 130 disconnects from the bias source 231 or after the charging electrode 333 disconnects from the bias source 331.

The voltage on the first reaction electrode 130 may be set to $V_0$ by any suitable method. For example, according to an embodiment, voltage on the first reaction electrode 130 may be set electrochemically by a portion 334 thereof. The portion 334 may have a chemical whose potential changes with changing chemical composition of the fluid 150. By making a change in the composition of the fluid 150, the voltage on the first reaction electrode 130 may be set to $V_0$. In another example, the portion 334 may change potential as a result of exposure to radiation such as light. By exposing the portion 334 to radiation, the voltage on the first reaction electrode 130 may be set to $V_0$.

Figure 2D:
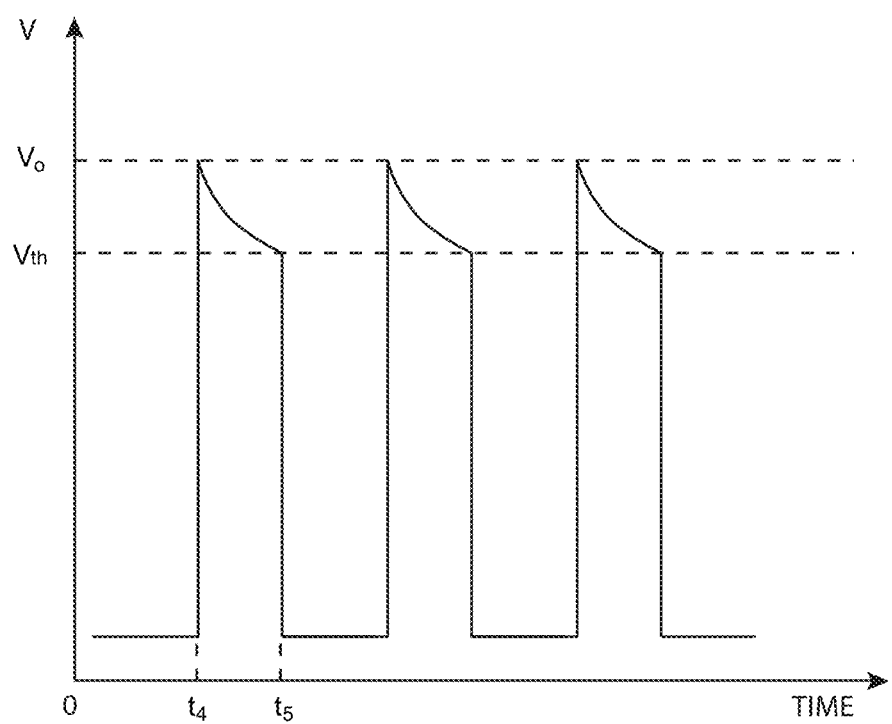
FIG. 2D shows an exemplary graph of the voltage of the first reaction electrode as a function of time in a periodic measurement.

FIG. 2D shows an exemplary graph of the voltage of the first reaction electrode 130 as a function of time, when the redox reaction discharges the capacitance 233 and the voltage of the first reaction electrode 130 is periodically reset to $V_0$. For example, the capacitance 233 is allowed to discharge at $t_4$ and the voltage of the first reaction electrode 130 is reset to $V_0$ at $t_5$. The rate of discharge of the first reaction electrode 130 may be measured from the difference between $V_{th}$ (voltage of the first reaction electrode 130 at $t_5$) and $V_0$. The rate of discharge of the first reaction electrode 130 may be measured by averaging the difference between $V_{th}$ and $V_0$ in multiple cycles.

Figure 3A:
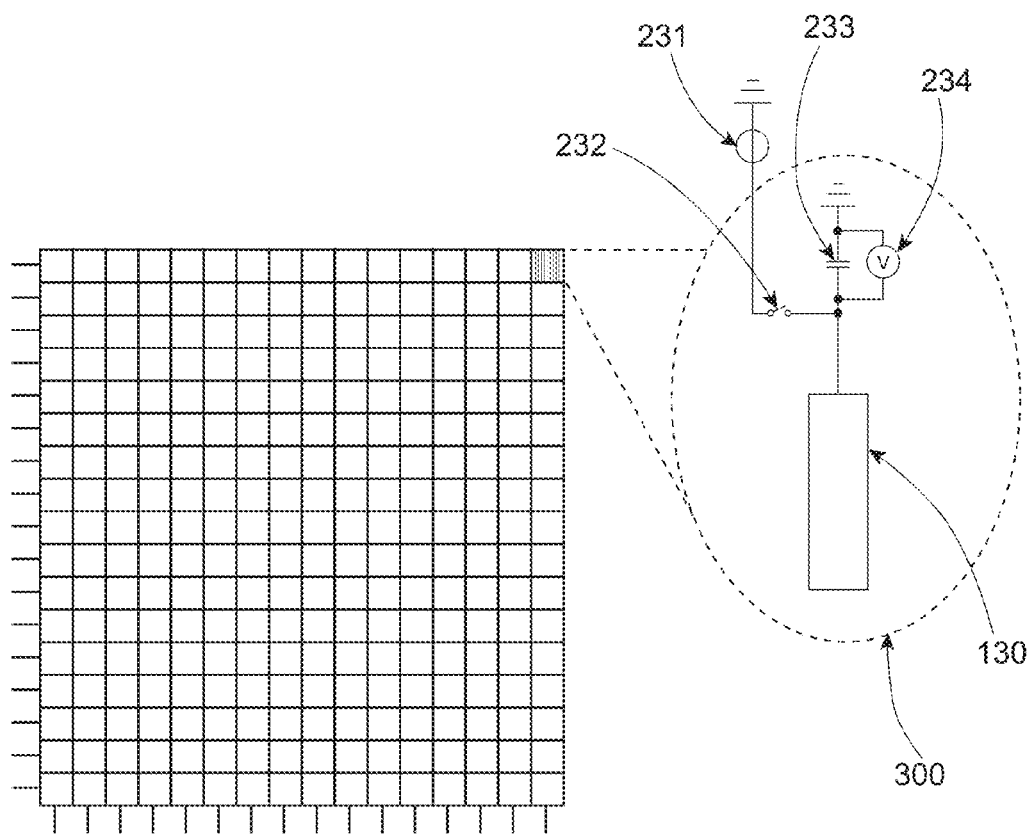
FIG. 3A shows an array of the circuitry in the dotted box 300 in FIG. 2A.
Figure 3B:
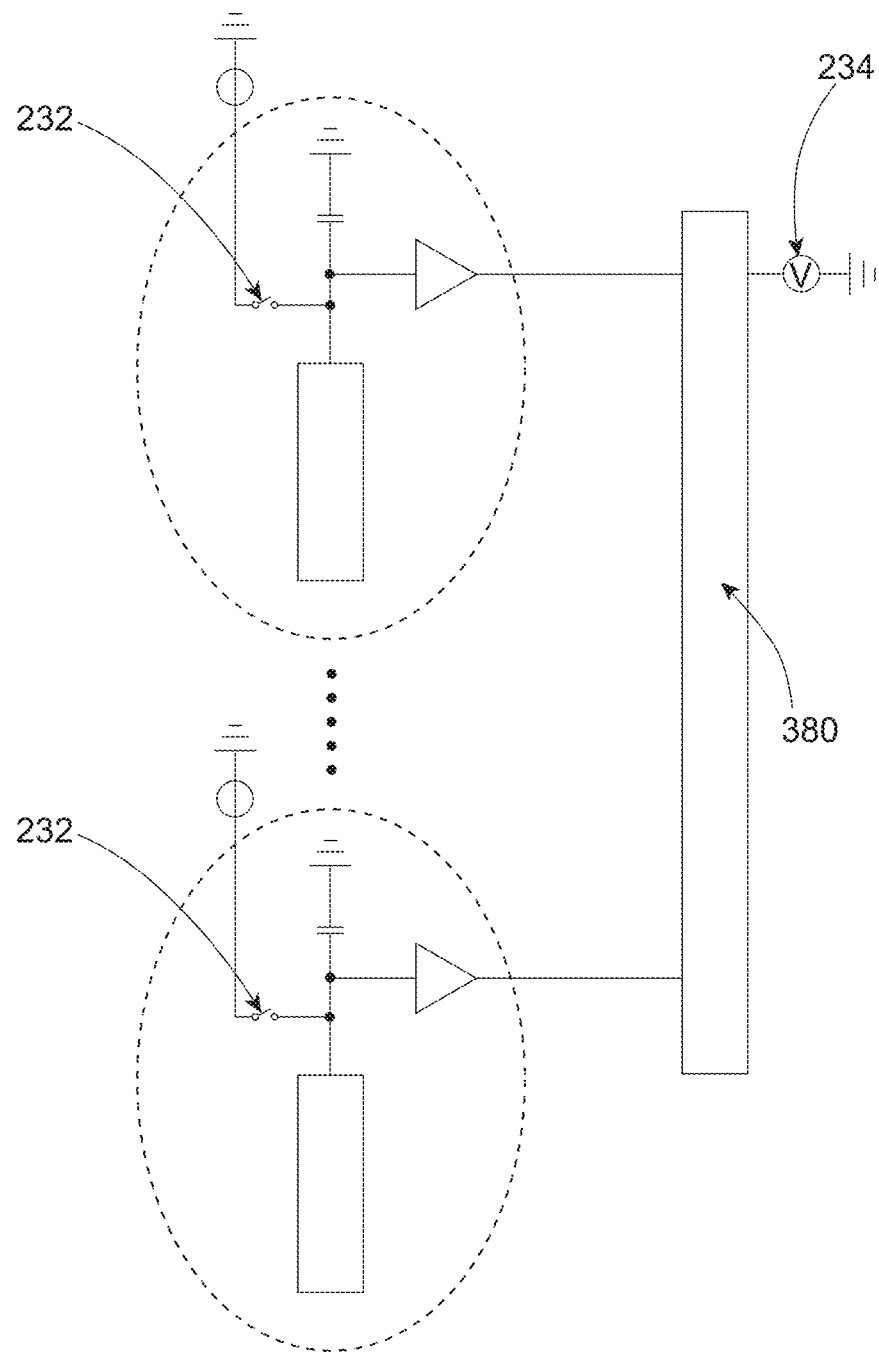
FIG. 3B shows that circuitry to measure the rate of charge or discharge of one of the electrodes may be shared in the array of FIG. 3A.

In an embodiment, the circuitry in the dotted box 300 in FIG. 2A or FIG. 2B, including the first reaction electrode 130 may be integrated in a microchip. In an embodiment, such a microchip may have a plurality of copies of the circuitry in the dotted box 300. These copies may be arranged in an array (e.g., a rectangular or hexagonal grid) such as the array shown in FIG. 3A (only the circuitry in the dotted box 300 is FIG. 2A is shown). Preferably, the bias source 231 is shared among these copies. For the purpose of this disclosure, a copy may be referred to as a "unit cell." In an embodiment as shown in FIG. 3A, a unit cell may have its own circuitry 234 (i.e., not shared with other unit cells) integrated in the unit cell. The measurements of the circuitry 234 in each may be transmitted to a bus through a multiplexer. In an embodiment depicted in FIG. 3B, the circuitry 234 may be shared among these copies through a multiplexer 390. A multiplexer (or MUX) is a device that selects one of several analog or digital input signals and forwards the selected input into a single line. In an embodiment, the circuitry 234 includes a high-impedance buffer configured to measure the voltage of the first reaction electrode 130 without discharging the capacitance 233. In an embodiment, the high-impedance buffer is included in each unit cell but other portions (such as A/D converter) of the circuitry 234 are shared among many unit cells through a multiplexer. In an embodiment, a unit cell comprises a memory configured to store the measurement by the circuitry 234 of the first reaction electrode 130. For example, the memory may be configured to measure and store the value of the voltage of the first reaction electrode 130 at $t_{int}$ or the time at which the voltage of the first reaction electrode 130 crossed a predetermined threshold value.

Figure 3C:
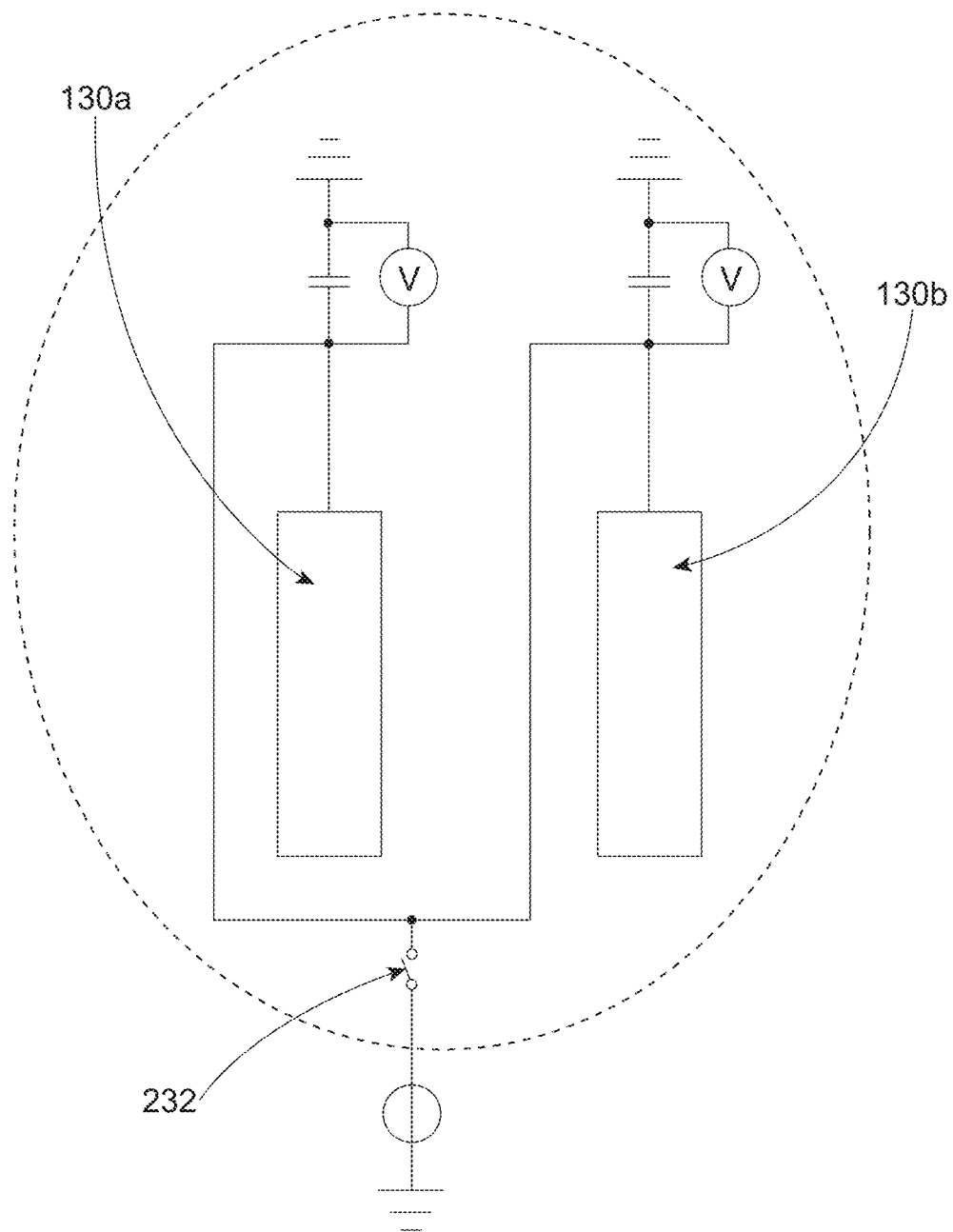
FIG. 3C shows an array of the circuitry in the dotted box 300 in FIG. 2A, except that a unit cellunit cell of the array has at least two electrodes, the rate of charging or discharging of capacitance of which are measured.

In an embodiment schematically shown in FIG. 3C, a unit cell may have at least two first reaction electrodes 130a and 130b. The first reaction electrodes 130a and 130b are arranged to be in vicinity of each other. As used in this disclosure, the word "vicinity" means distance no greater than the diffusion length of the analyte at $t_{int}$. Correlation of the voltages on the first reaction electrodes 130a and 130b may be used to determine the validity of data collected from this unit cell. For example, if the voltages on the first reaction electrodes 130a and 130b differ by a threshold value, data collected from this unit cell is considered invalid and discarded.

Figure 3D:
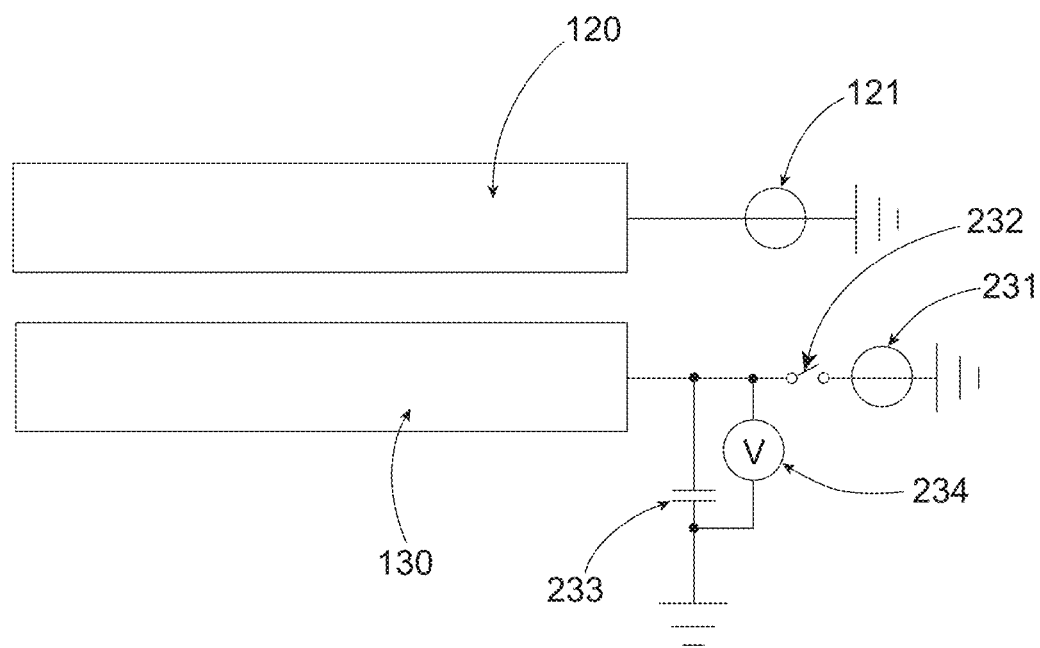
FIG. 3D shows an array of the circuitry in the dotted box 300 in FIG. 2A, except that a unit cellunit cell of the array has another biased electrode integrated in the unit cell.

In an embodiment schematically shown in FIG. 3D, a unit cell may have the second reaction electrode 120 integrated in the unit cell. In an embodiment, the second reaction electrode 120 can be shared among more than one unit cell.

In an embodiment, a unit cell has an area from 0.01 to 100 $\mu m^2$, such as about 1 $\mu m^2$. In one embodiment, the array has more than 100 unit cells, $10^6$ unit cells, or $10^{10}$ unit cells. In an embodiment, the unit cells do not comprise a photodiode.

Figure 4A:
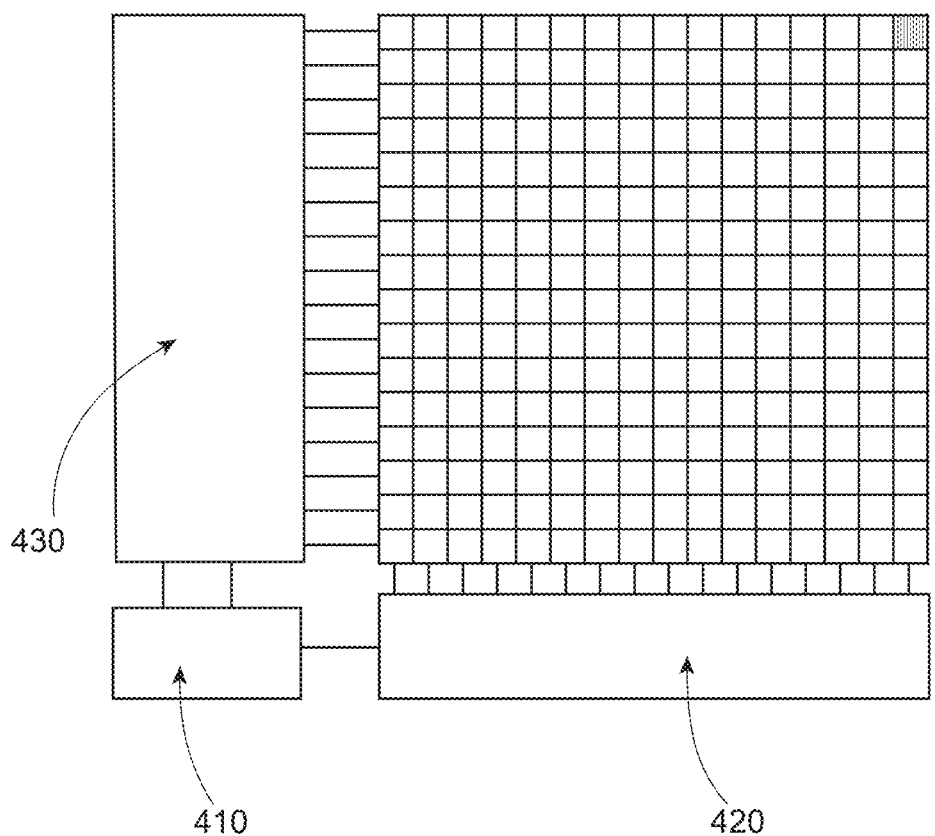
FIG. 4A shows an exemplary embodiment of the array.
Figure 4B:
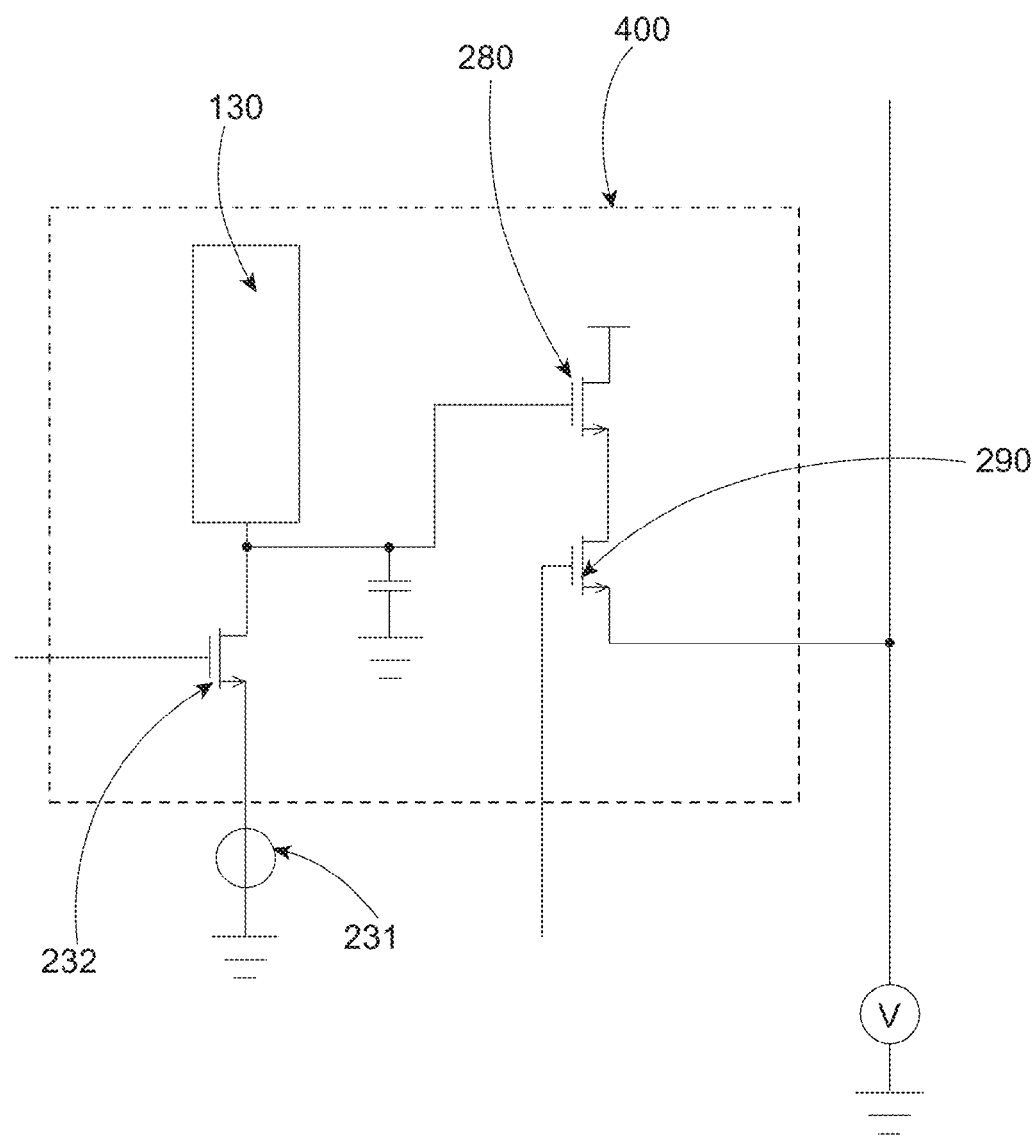
FIG. 4B shows an exemplary schematic of a unit cell in the array of FIG. 4A.

FIG. 4A shows an exemplary embodiment of the array of unit cells. The unit cells may be interrogated by enabling a row of unit cells using row decoder 430 which connects the unit cells to a shared A/D converter by enabling a switch (e.g., a transistor 290 in FIG. 4B). 420 may be an array of A/D converters (one for each column of unit cells) or a multiplexer that connects the column outputs to one or more shared A/D converters. 420 and 430 are under control of a controller 410. FIG. 4B shows an exemplary schematic of a unit cell 400 in the array of FIG. 4A. The unit cell 400 may have as few as three transistors 290, 280 and 232. Other circuitry is shared among the unit cells, which allows the footprint of the unit cell 400 to be reduced. The multiplexing functionality may be provided by transistor 290. Transistor 280 may act as a voltage buffer to read the voltage at electrode 130 without discharging the capacitance of electrode 130. Switch 232 may be implemented as a transistor. The functionality provided by switch 232, transistors 280 and 290 can be implemented using different electronic devices than shown as examples in FIG. 4B. One row of unit cells in the array may be interrogated at a time, and the entire array may be interrogated by interrogating each row of unit cells. Furthermore, the entire array can be interrogated multiple times to obtain the information such as that contained in FIG. 2B.

Figure 4C:
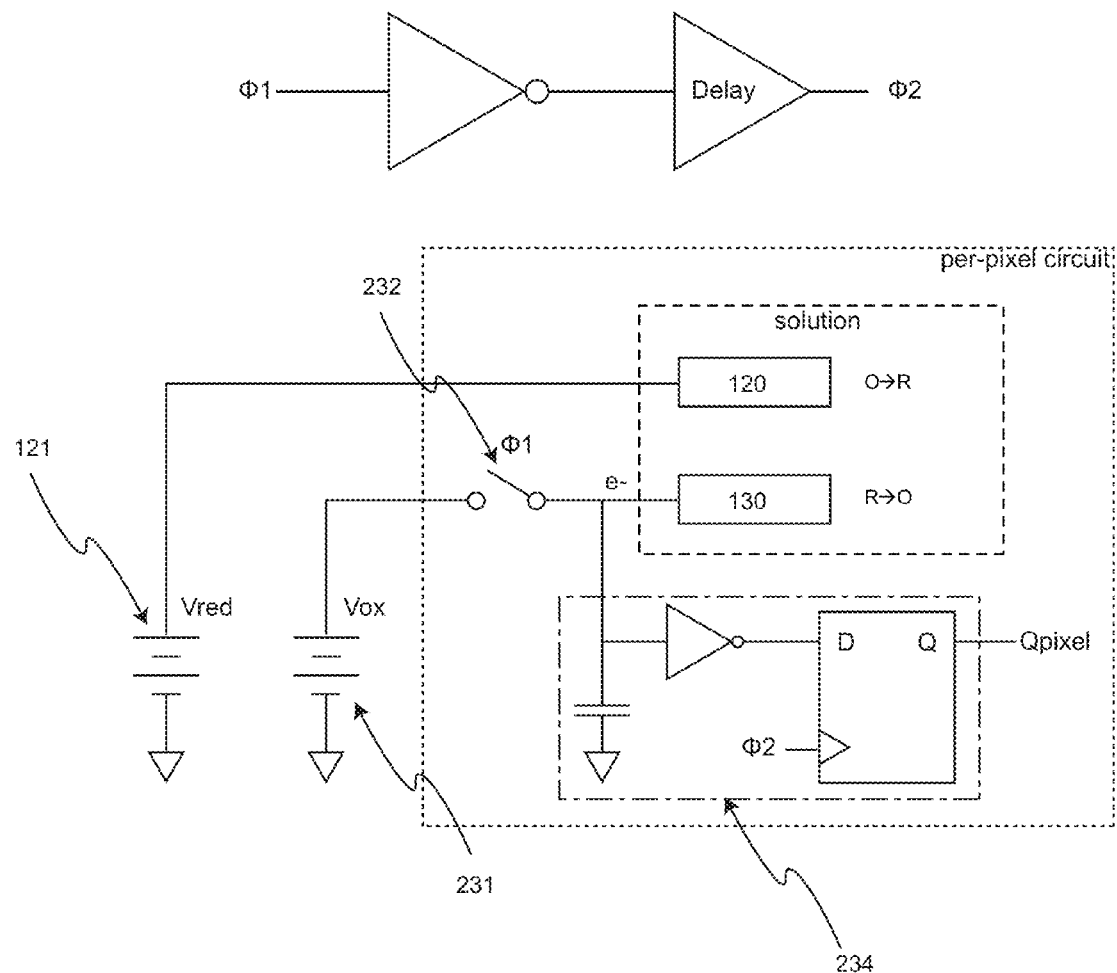
FIG. 4C shows an exemplary schematic of a unit cell in the array of FIG. 4A.

FIG. 4C shows an implementation of a unit cell of the array, where the unit cell has both the first reaction electrode 130 and the second reaction electrode 120 in the unit cell, as shown in FIG. 3D. In this example, switch 232 is controlled by a clock $\phi 1$. The circuitry 234 may include an inverting amplifier and a D flip-flop controlled by a clock $\phi 2$. $\phi 2$ may be delayed from $\phi 1$ by a fixed amount. Circuitry 234 may be in the unit cell or shared among unit cells.

Figure 4D:
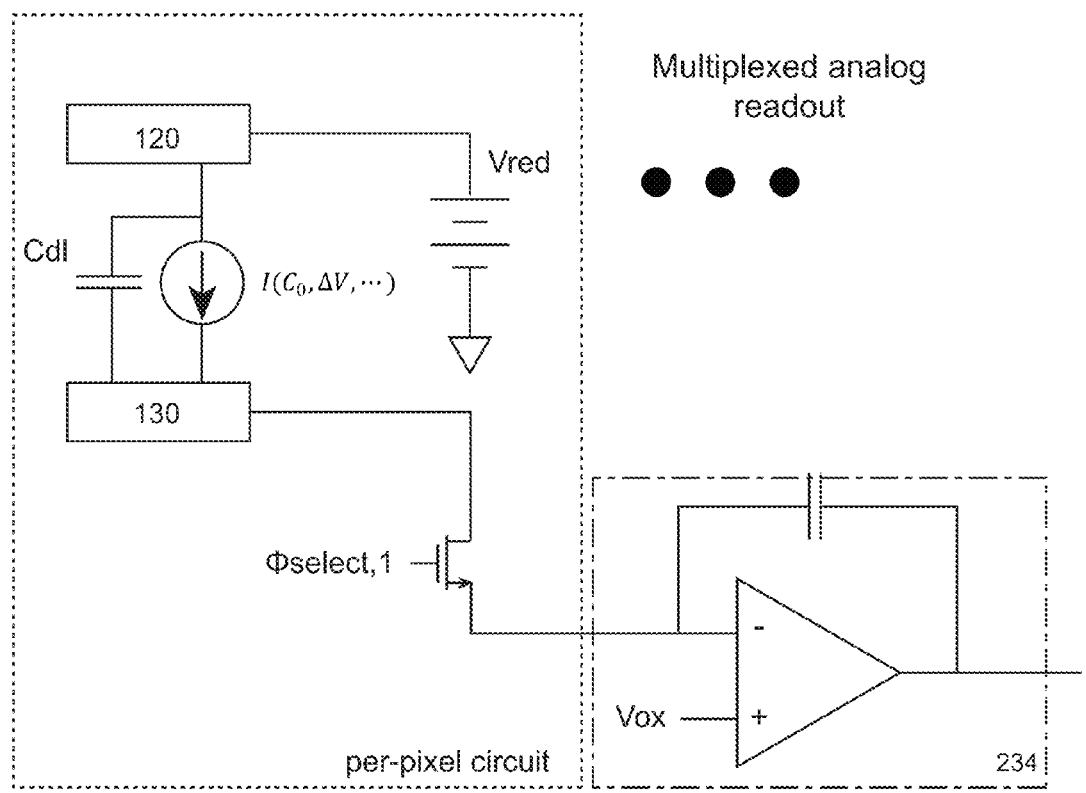
FIG. 4D shows an exemplary schematic of a unit cell in the array of FIG. 4A.

FIG. 4D shows another implementation of a unit cell of the array, where the unit cell has both the first reaction electrode 130 and the second reaction electrode 120 in the unit cell, as shown in FIG. 3D. In this example, the unit cell may have only one transistor controlled by a select signal $\phi_{select,1}$, and circuitry 234 is shared among multiple unit cells. This implementation may allow the footprint of the unit cell to be very small and the density of the array very high. The circuitry 234 may have an integrating amplifier, which allows direct measurement of the amount of charge flowed through the first reaction electrode 130.

Figure 4E:
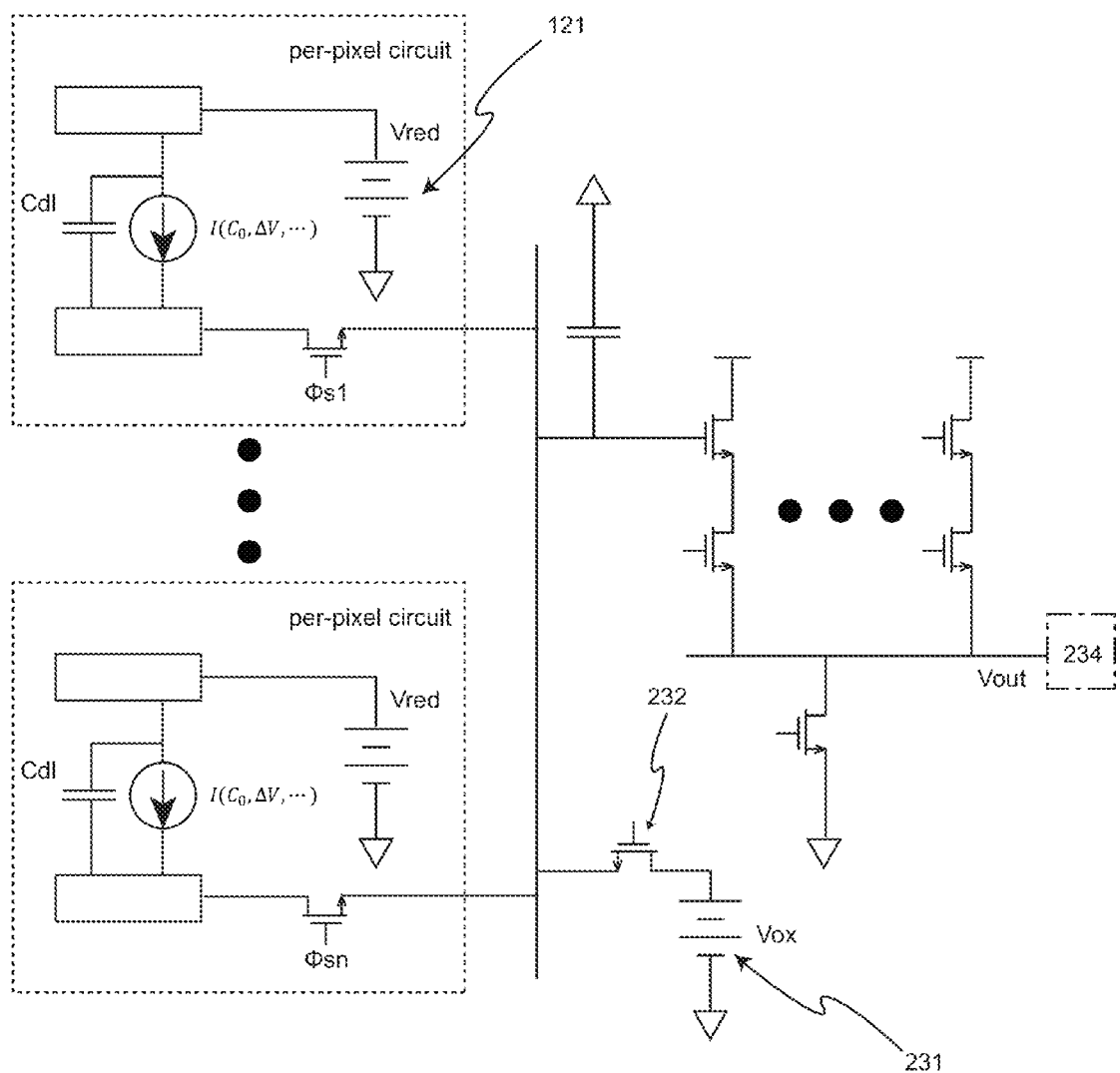
FIG. 4E shows an exemplary schematic of a unit cell in the array of FIG. 4A.

FIG. 4E shows yet another implementation of f the array, where each unit cell may have as few as one transistor that controllably connects the first electrode in the unit cell to a bus. The bias source 231 is also connected to the bus through the switch 232. Circuitry 234 and the bias source 231 may be shared among all unit cells in the array, which allows the footprint of the unit cell to be very small and the density of the array very high.

Other suitable circuitry may be used in the array.

Figure 5:
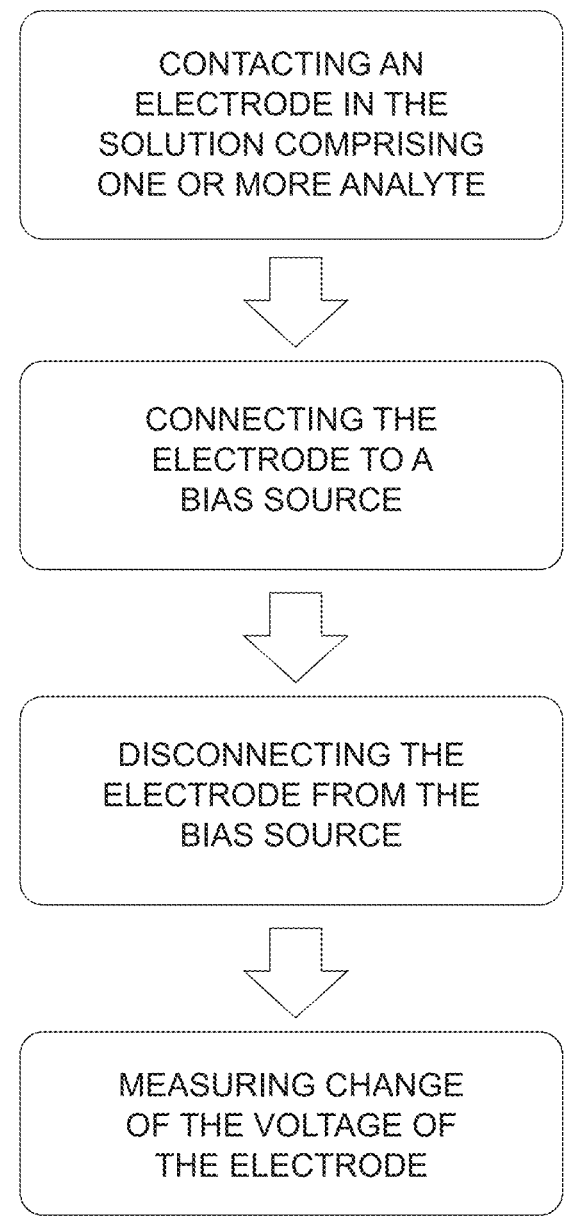
FIG. 5 shows a flowchart of a method of operating the array of FIG. 4A.

In an embodiment, as schematically shown in the flowchart of FIG. 5, a method of operating the array comprises: contacting the first reaction electrode 130 to the fluid 150 comprising one or more analyte; connecting the first reaction electrode 130 to the bias source 231, such that the voltage of the first reaction electrode 130 is substantially at the voltage $V_0$ of the bias source 231; disconnecting the first reaction electrode 130 from the bias source 231; measuring change of the voltage of the first reaction electrode 130, wherein the change of the voltage is produced from charging or discharging of capacitance of the first reaction electrode 130 due to redox reactions in the vicinity of the first reaction electrode 130. The method may further comprise storing the change of the voltage of the first reaction electrode 130 in a memory.

Figure 6:
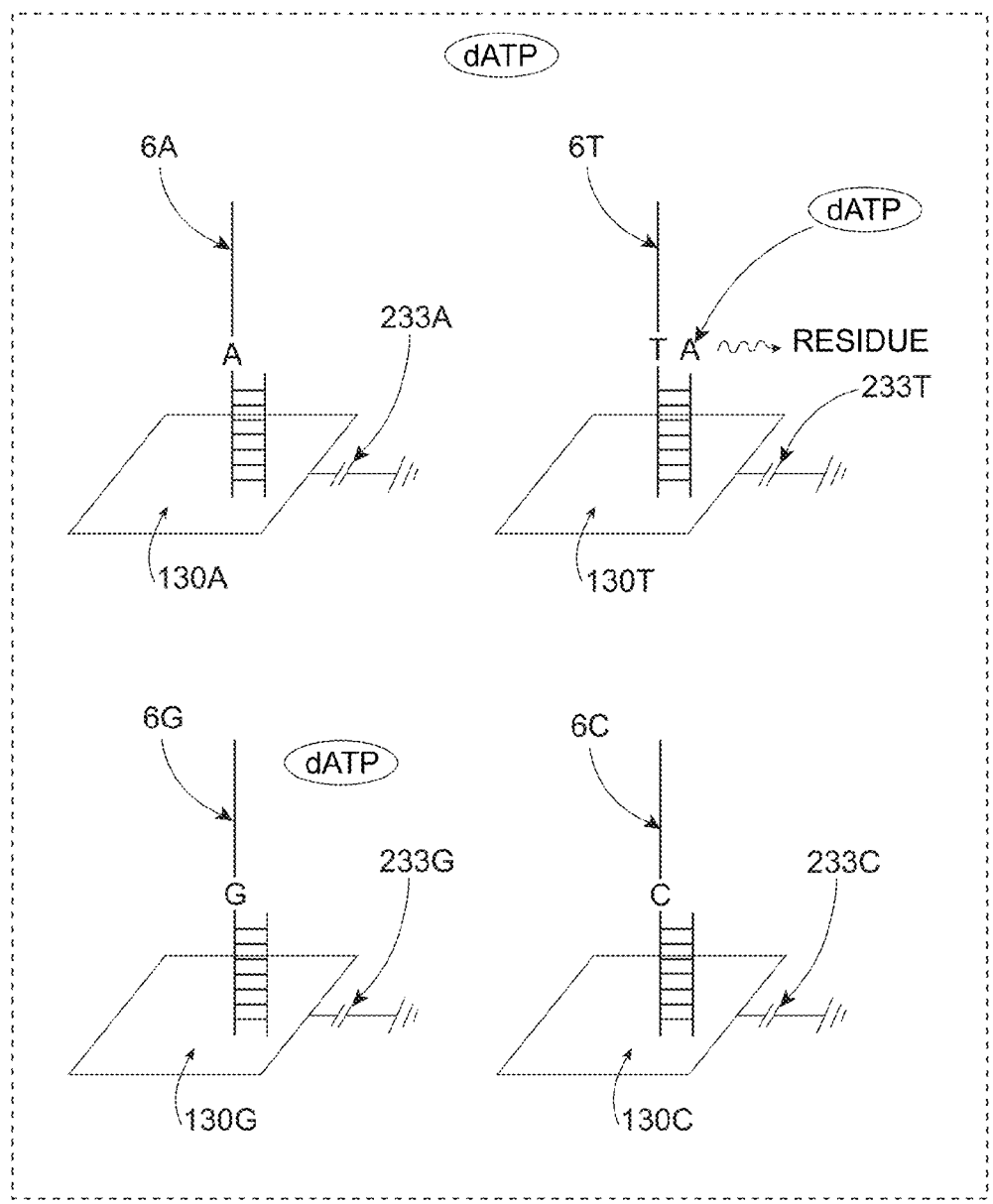
FIG. 6 shows an exemplary scheme to sequence DNA with the array of FIG. 4A.

An exemplary method of using the array to sequence DNA may comprise the following. A unit cell of the array may have one or more copies of a DNA molecule to be sequenced attached to or in proximity of the first reaction electrodes 130 therein, or the second reaction electrode 120 if the unit cell has its own second reaction electrode 120 (i.e., the second reaction electrode 120 not shared with other unit cells), the DNA molecule to be sequenced having a primer hybridized thereto. The unit cell preferably does not have DNA molecules of more than one sequence. The array is in contact with the fluid 150. The fluid 150 comprises reagents such as polymerase, and salt (e.g., $MgCl_2$). Only one type of nucleoside triphosphate (i.e., one type among deoxyadenosine triphosphate (dATP), deoxyguanosine triphosphate (dGTP), deoxythymidine triphosphate (dTTP) and deoxycytidine triphosphate (dCTP)) is added to the fluid 150. The nucleoside triphosphate may be in its natural form or modified with a moiety that can undergo a redox reaction in the fluid 150. Alternatively, only one type of nucleoside polyphosphates (i.e., one type among deoxyadenosine polyphosphates, deoxyguanosine polyphosphates, deoxythymidine polyphosphates and deoxycytidine polyphosphates) is added to the fluid 150. The fluid 150 is set to a temperature suitable for the polymerase to incorporate the nucleoside triphosphate into the one or more DNA primers. Only unit cells with DNA molecules whose next unpaired base is complementary to the added nucleoside triphosphate will have the nucleoside triphosphate incorporated to the primers. For example, as illustrated in FIG. 6, in which dATP is added into fluid 150 as the nucleoside triphosphate, four unit cells each with a first reaction electrode (130, 130T, 130G and 130C) is shown. On first reaction electrodes 130, 130T, 130G and 130C DNA molecules 6A, 6T, 6G and 6C are respectively attached. Each of these DNA molecules has a primer being extended by the polymerase. On DNA molecules 6A, 6T, 6G and 6C, the next unpaired bases are A, T, G and C, respectively. The dATP in the fluid 150 will thus only be incorporated to the primer on the DNA molecule 6A. The polymerase splits the terminal phosphate groups (with or without the moiety) from the incorporated dATP. The terminal phosphate groups split from nucleoside triphosphate is often referred to as phosphate residue. The phosphate residue and/or the moiety undergoes redox reaction in the vicinity of the first reaction electrode 130T. As a result, capacitance 233T of the first reaction electrode 130T charges or discharges at a rate beyond that caused by leakage current (e.g., trace 291 in FIG. 2B). Since no incorporation of dATP to the primers on the other three first reaction electrodes 130, 130G and 130C, capacitance 233A, 233G and 233C of these first reaction electrodes 130, 130G and 130C do not charges or discharges at a rate beyond that caused by leakage current. The difference between the rate of charge of discharge on the first reaction electrodes 130, 130T, 130G and 130C indicates that the next unpaired base on DNA 6T is thymine. Fluid 150 is removed and the array is washed to remove any residue of fluid 150. These steps are repeated with the other three nucleoside triphosphates to complete sequencing of all the DNA molecules on the unit cells of the array. Alternatively, more than one type of nucleoside triphosphate modified with different moieties may be added to the fluid 150. The electrodes 130, 130T, 130G and 130C may detect that the next unpaired base thereon by detecting the rate of charge of discharge on these electrodes respectively, caused by redox reactions of the different moieties on the nucleoside triphosphate. Other DNA sequencing methods that can be applied to the array include those disclosed in U.S. patent application Ser. No. 11/967,600, titled "Electronic Sensing for Nucleic Acid Sequencing," filed Dec. 31, 2007, the disclosures of which are incorporated herein by reference in its entirety.

Disclosed herein is a device suitable for detecting chemical reaction in a fluid phase comprising: a plurality of first reaction electrodes arranged in an array, the plurality of first reaction electrodes configured to be exposed to a fluid and having a capacitance; first circuitry configured to controllably set the plurality of first reaction electrode to a predetermined voltage and allow the capacitance of the plurality of first reaction electrode to charge or discharge through the fluid; and second circuitry configured to measure a rate of charging or discharging of the capacitance of the plurality of first reaction electrodes.

According to an embodiment, the capacitance includes self-capacitance of the plurality of first reaction electrodes and capacitance of interfaces between the plurality of first reaction electrodes and the fluid.

According to an embodiment, the charging or discharging of the capacitance is caused by redox reactions in the fluid.

According to an embodiment, the device further comprises a reference electrode with a fixed reduction potential to the fluid.

According to an embodiment, the reference electrode is selected from the group consisting of standard hydrogen electrode (SHE), normal hydrogen electrode (NHE), reversible hydrogen electrode (RHE), saturated calomel electrode (SCE), copper-copper (II) sulfate electrode (CSE), silver-silver chloride (Ag/AgCl) electrode, silver pseudoreference electrode, and quasi-reference (QRE).

According to an embodiment, the device further comprises a second reaction electrode configured to be electrically biased relative to the fluid.

According to an embodiment, the second reaction electrode is not consumed.

According to an embodiment, the plurality of first reaction electrodes are a material that is not consumed by the fluid.

According to an embodiment, the first circuitry comprises a switch.

According to an embodiment, the second circuitry is configured to measure the rate of charging or discharging of the capacitance by measuring a voltage of the plurality of first reaction electrodes as a function of time.

According to an embodiment, the first circuitry is configured to controllably set the plurality of first reaction electrode to the predetermined voltage and allow the capacitance of the plurality of first reaction electrode to charge or discharge through the fluid by controllably connecting the plurality of first reaction electrodes to a bias source and controllably disconnecting the plurality of first reaction electrodes from the bias source.

According to an embodiment, the first circuitry is configured to controllably set the plurality of first reaction electrode to the predetermined voltage and allow the capacitance of the plurality of first reaction electrode to charge or discharge through the fluid by controllably changing voltage of a charging electrode exposed to the fluid, by e.g. controllably connecting the charging electrode to a bias source and controllably disconnecting the charging electrode from the bias source, wherein the charging electrode is configured to affect the voltage on the plurality of first reaction electrodes.

According to an embodiment, the second circuitry is configured to measure the rate of charging or discharging of the capacitance by measuring an amount of voltage change from the predetermined voltage at a time point.

According to an embodiment, the second circuitry is configured to measure the rate of charging or discharging of the capacitance by measuring an amount of time for a voltage of the plurality of first reaction electrodes to change from the predetermined voltage o by a predetermined amount.

According to an embodiment, the device is a microchip.

According to an embodiment, the second circuitry is configured to measure the voltage of the plurality of first reaction electrodes without discharging the capacitance.

According to an embodiment, the second circuitry comprises a memory.

According to an embodiment, the device further comprises a multiplexer and a controller.

According to an embodiment, the device further comprises at least one second reaction electrode in vicinity of at least one of the plurality of first reaction electrodes.

According to an embodiment, the first reaction electrodes and/or the second reaction electrodes are coated with an organic or inorganic coating.

According to an embodiment, a geometric area of each of the first reaction electrodes is between 0.01 $\mu m^2$ and 100 $\mu m^2$.

According to an embodiment the plurality of first reaction electrodes comprises between 100 and 10,000,000,000 first reaction electrodes; and the first circuitry comprises a plurality of measurement circuits, each of which corresponding to one of the plurality of first reaction electrodes.

According to an embodiment, the second circuitry is shared among more than one first electrodes in the plurality of first electrodes.

According to an embodiment, the first reaction electrodes are selected from the group consisting of platinum, gold, indium tin oxide, diamond-like carbon doped with impurities, glassy carbon, silver, carbon nanotube, graphene, conducting polymers; and/or wherein the second reaction electrodes are selected from the group consisting of platinum, gold, indium tin oxide, diamond-like carbon doped with impurities, glassy carbon, silver, carbon nanotube, graphene, conducting polymers.

Also disclosed herein is a method comprising: contacting an electrode to a fluid; setting a voltage of the electrode to a predetermined voltage; allowing the electrode to charge or discharge through the fluid; and measuring change of the voltage of the electrode.

According to an embodiment, change of the voltage of the electrode is produced from charging or discharging of capacitance of the electrode.

According to an embodiment, the charging or discharging of capacitance of the electrode is caused by redox reactions in a vicinity of the electrode.

According to an embodiment, the method further comprises storing the change of the voltage of the electrode in a memory.

According to an embodiment, the method further comprises repeating steps of contacting, connecting, disconnecting and measuring on at least 100 electrodes.

According to an embodiment, setting the voltage of the electrode is by connecting the electrode to a bias source.

According to an embodiment, allowing the electrode to charge or discharge is by disconnecting the electrode from the bias source.

According to an embodiment, setting the voltage of the electrode is by connecting a charging electrode exposed to the fluid to a bias source.

According to an embodiment, allowing the electrode to charge or discharge is by disconnecting the charging electrode from the bias source.

According to an embodiment, setting the voltage of the electrode is by changing a composition of the fluid.

According to an embodiment, setting the voltage of the electrode is by exposing the electrode to a radiation.

Also disclosed herein is a method comprising: contacting a plurality of electrodes to a fluid, each of the plurality of electrodes having a DNA molecule attached thereto or in proximity thereof, wherein DNA molecule has a primer hybridized thereto; adding at least one type of nucleoside polyphosphate (tri-, tetra-, penta-phosphate, etc.) to the fluid; setting the fluid to a temperature suitable for the one type of nucleoside triphosphate to be incorporated into at least some of the primers; measuring a rate of charge or discharge of capacitance of each of the plurality of electrodes.

According to an embodiment, the method further comprises removing the fluid and washing the plurality of electrodes.

According to an embodiment, a device comprises a plurality of first reaction electrodes arranged in an array, the plurality of first reaction electrodes configured to be exposed to a fluid and having a capacitance; means for controllably setting the plurality of first reaction electrode to a predetermined voltage and allowing the capacitance of the plurality of first reaction electrode to charge or discharge through the fluid; means for measuring a rate of charging or discharging of the capacitance of the plurality of first reaction electrodes.

According to an embodiment, a system comprises any of the device disclosed, a processor, a memory, and a communication interface.

While various aspects and embodiments have been disclosed herein, other aspects and embodiments will be apparent to those skilled in the art. Various components of the disclosed devices and various steps of the disclosed methods may be combined in any suitable combination. The various aspects and embodiments disclosed herein are for purposes of illustration and are not intended to be limiting, with the true scope and spirit being indicated by the following claims.

We claim:

1. A device suitable for detecting chemical reaction in a fluid phase, comprising:
    a plurality of first reaction electrodes arranged in an array, the plurality of first reaction electrodes configured to be exposed to a fluid and having a capacitance;
    first circuitry configured to controllably set the plurality of first reaction electrode to a predetermined voltage and allow the capacitance of the plurality of first reaction electrode to charge or discharge through the fluid; and
    second circuitry configured to measure a rate of charging or discharging of the capacitance of the plurality of first reaction electrodes.

2. The device of claim 1, wherein the capacitance includes self-capacitance of the plurality of first reaction electrodes and capacitance of interfaces between the plurality of first reaction electrodes and the fluid.

3. The device of claim 1, wherein the charging or discharging of the capacitance is caused by redox reactions in the fluid.

4. The device of claim 1, further comprising a reference electrode with a fixed reduction potential to the fluid.

5. The device of claim 4, wherein the reference electrode is selected from the group consisting of standard hydrogen electrode (SHE), normal hydrogen electrode (NHE), reversible hydrogen electrode (RHE), saturated calomel electrode (SCE), copper-copper(II) sulfate electrode (CSE), silver-silver chloride (Ag/AgCl) electrode, silver pseudoreference electrode, and quasi-reference (QRE).

6. The device of claim 1, wherein the first circuitry comprises a switch.

7. The device of claim 1, wherein the second circuitry is configured to measure the rate of charging or discharging of the capacitance by measuring a voltage of the plurality of first reaction electrodes as a function of time.

8. The device of claim 1, wherein the first circuitry is configured to controllably set the plurality of first reaction electrode to the predetermined voltage and allow the capacitance of the plurality of first reaction electrode to charge or discharge through the fluid by controllably connecting the plurality of first reaction electrodes to a bias source and controllably disconnecting the plurality of first reaction electrodes from the bias source.

9. The device of claim 1, wherein the first circuitry is configured to controllably set the plurality of first reaction electrode to the predetermined voltage and allow the capacitance of the plurality of first reaction electrode to charge or discharge through the fluid by controllably changing voltage of a charging electrode exposed to the fluid, wherein the charging electrode is configured to affect the voltage on the plurality of first reaction electrodes.

10. The device of claim 1, wherein the second circuitry is configured to measure the rate of charging or discharging of the capacitance by measuring an amount of voltage change from the predetermined voltage at a time point.

11. The device of claim 1, wherein the second circuitry is configured to measure the rate of charging or discharging of the capacitance by measuring an amount of time for a voltage of the plurality of first reaction electrodes to change from the predetermined voltage o by a predetermined amount.

12. The device of claim 7, wherein the second circuitry is configured to measure the voltage of the plurality of first reaction electrodes without discharging the capacitance.

13. The device of claim 1, further comprising at least one second reaction electrode in vicinity of at least one of the plurality of first reaction electrodes.

14. The device of claim 1, wherein a geometric area of each of the first reaction electrodes is between 0.01 $\mu m^2$ and 100 $\mu m^2$.

15. The device of claim 1, wherein the plurality of first reaction electrodes comprises between 100 and 10,000,000,000 first reaction electrodes; and the first circuitry comprises a plurality of measurement circuits, each of which corresponding to one of the plurality of first reaction electrodes.

16. The device of claim 1, wherein the second circuitry is shared among more than one first electrodes in the plurality of first electrodes.

17. The device of claim 1, wherein the first reaction electrodes are selected from the group consisting of platinum, gold, indium tin oxide, diamond-like carbon doped with impurities, glassy carbon, silver, carbon nanotube, graphene, and conducting polymers; and/or wherein the second reaction electrodes are selected from the group consisting of platinum, gold, indium tin oxide, diamond-like carbon doped with impurities, glassy carbon, silver, carbon nanotube, graphene, and conducting polymers.

18. The device of claim 1, wherein the second circuitry is configured to measure a total amount of charge accumulated on the capacitance during a predetermined time interval.

* * * * *